United States Patent [19]

Wu et al.

[11] Patent Number: 6,166,156

[45] Date of Patent: Dec. 26, 2000

[54] METHOD FOR MAKING PHOTOCURABLE HALOFLUORINATED ACRYLATES

[76] Inventors: Chengjiu Wu, 4 Tree Top Ter., Morristown, N.J. 07960; Baopei Xu, 191 Dafrack Dr., Lake Hiawatha, N.J. 07034; James T. Yardley, 40 Macculloch Ave., Morristown, N.J. 07960

[21] Appl. No.: 09/190,194

[22] Filed: Nov. 12, 1998

[51] Int. Cl.$^7$ .......................... C08F 20/22; C08F 120/22; C08F 6/00; C08F 220/22

[52] U.S. Cl. .......................... 526/245; 526/914; 528/489; 528/495; 528/496; 522/182; 570/124; 570/125; 570/138; 570/155; 570/156; 570/157; 570/158

[58] Field of Search .................... 522/182, 187; 526/245, 914; 528/489, 495, 496; 570/124, 125, 138, 134, 155, 156, 157, 158, 173, 175

[56] References Cited

U.S. PATENT DOCUMENTS

| | | | |
|---|---|---|---|
| 3,147,314 | 9/1964 | Cluff . | |
| 4,122,288 | 10/1978 | Christensen et al. | 568/775 |
| 4,356,296 | 10/1982 | Griffith et al. | 526/242 |
| 4,732,843 | 3/1988 | Budde et al. | 526/245 |
| 4,820,588 | 4/1989 | Brinduse et al. | 428/422 |
| 5,024,507 | 6/1991 | Minns et al. | 385/145 |
| 5,238,974 | 8/1993 | Yamamoto et al. | 522/75 |
| 5,333,234 | 7/1994 | Hashimoto et al. | 385/145 |

FOREIGN PATENT DOCUMENTS

| | | |
|---|---|---|
| 195565 | 9/1986 | European Pat. Off. . |
| 190705 | 10/1959 | France . |
| WO 98/12163 | 8/1964 | WIPO . |
| WO 98/46556 | 10/1998 | WIPO . |

OTHER PUBLICATIONS

Paciorek, K. L., et al., Mechanism of Amine Crosslinking of Fluoroelastomers. I. Solution Studies, *Journal of Polymer Science*, vol. XLV, 405–413 (1960).

Boutevin, B., et al., New Halogenated Monomers and Polymers for Low Loss Plastic Optical Fiber, *Fiber and Integrated Optics*, vol. 13, 309–319 (1994).

Turri, Stefano, et al., End Group Chemistry of Fluoro–Oligomers: Highly Selective Syntheses of Diepoxy, Diallyl, and Tetraol Derivatives, *Journal of Polymer Science: Part A: Polymer Chemistry*, vol. 34, 3263–3275 (1996).

*Primary Examiner*—Susan W. Berman

[57] ABSTRACT

Halofluorinated alkylene monomers are made by a method comprising the steps of: (a) subjecting a first polymer which is the reaction product of a fluorinated vinyl monomer and a vinyl comonomer to dehydrohalogenation to form a second polymer; (b) treating the second polymer with an oxidizing agent to form an oxidation product consisting of a α, ω-dicarboxylic acid or an ester derivative thereof; and (c) treating said oxidation product with a reducing agent to form a reduction product consisting of a a α, ω-diol. Preferably, the first polymer has a structure of $-\!\![CH_2CYZ(CF_2CFX)_n]_m\!\!-$ wherein X and Y=F, Cl or Br; X and Y may be the same or different; Z=H, F, Cl, Br, alkyl or perfluoroalkyl containing from about 1 to about 10 carbon atoms; n=an integer larger than about 1; and m is an integer between about 2 and about $10^5$. The α, ω-dicarboxylic acids and α, ω-diols produced herein can be directly used as polycondensation monomers. Alternatively, the α, ω-dicarboxylic acids and α, ω-diols can be further derivitized to tri-, tetra- or other multifunctional alcohols which may be directly used as condensation monomers or they may be converted to acrylates which may be photocured in the presence of a radical photoinitiator into transparent polymers which are useful as optical waveguiding materials.

22 Claims, No Drawings

METHOD FOR MAKING PHOTOCURABLE HALOFLUORINATED ACRYLATES

BACKGROUND OF THE INVENTION

1. Field of the Invention

This invention relates to halofluorinated monomers; and more particularly to a method for making halofluorinated monomers.

2. Description of the Prior Art

The production of optical waveguiding structures by photocuring commercially available multifunctional acrylates containing C, H, O, and N atoms is well known. Such structures, however, exhibit high optical loss at the near infrared region due to the inherent absorption of the C—H bond. Replacing the C—H by C—F bonds results in reduced optical loss, but the refractive index of the resulting photopolymer becomes undesirably low. One approach to alleviate this problem has been the replacement of a portion of the fluorine atoms of the fluoroalkylene moiety with heavier halogen atoms such as chlorine and bromine, both of which are known to increase refractive indices.

In many instances, the processes for making the foregoing halogen-substituted fluorinated acrylates can be quite cumbersome. It would therefore be desirable to provide an improved process for making modified fluorinated monomers for interconnect applications which can be photocured to form optical waveguide structures possessing low optical loss and having increased adhesion. Additionally, it would be desirable if such modified fluorinated monomers would have a refractive index value approaching that of traditional optical fibers.

SUMMARY OF THIS INVENTION

In accordance with this invention, there is provided a method for making halofluorinated multifunctional monomers which comprises the steps of: (a) subjecting a first polymer which is the reaction product of a fluorinated vinyl monomer and a vinyl comonomer to dehydrohalogenation to form a second polymer; (b) treating the second polymer with an oxidizing agent to form an oxidation product consisting of a α, ω-dicarboxylic acid or an ester derivative thereof; and (c) treating said oxidation product with a reducing agent to form a reduction product consisting of a α, ω-diol. Preferably, the first polymer has a structure of —[CH$_2$CYZ(CF$_2$CFX)$_n$]$_m$— wherein X and Y=F, Cl or Br; X and Y may be the same or different; Z=H, F, Cl, Br, or an alkyl or perfluoroalkyl containing from about 1 to about 10 carbon atoms; n=an integer larger than about 1; and m is an integer between about 2 and about $10^5$. The intermediate α, ω-dicarboxylic acid or ester derivatives thereof and the α, ω-diol compounds may be used directly as polymerization monomers or they may be further synthesized into tri-, tetra-, and other multifunctional alcohols which also may be used as polymerization monomers. Alternatively, these multifunctional alcohols may be further derivitized to acrylates which may be photocured to form transparent polymers which are useful as optical waveguiding materials.

Advantageously, the method disclosed and claimed herein is economical and efficient to practice. Moreover, the novel halofluorinated monomers produced in accordance with the teachings of the present invention exhibit superior optical waveguiding characteristics over the halofluorinated monomers of the prior art.

DESCRIPTION OF THE PREFERRED EMBODIMENTS

The method for preparing the halofluorinated multifunctional monomers of the present invention may be represented by the following scheme:

1. Dehydrohalogenation

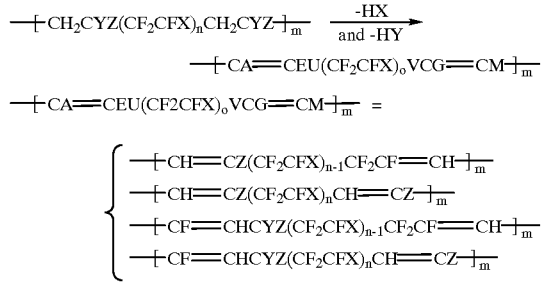

2. Oxidation

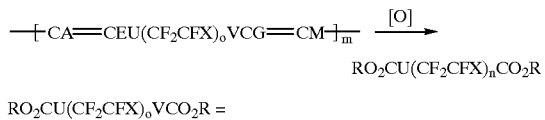

3. Reduction

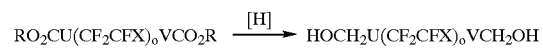

4. Derivitization

HOCH$_2$U(CF$_2$CFX)$_o$VCH$_2$OH ⟶

HOCH$_2$U(CF$_2$CFX)$_o$VCH$_2$OCH$_2$CH(OH)CH$_2$OH

HOCH$_2$U(CF$_2$CFX)$_o$VCH$_2$OH ⟶

HOCH$_2$CH(OH)CH$_2$OCH$_2$(CF$_2$CFX)$_o$VCH$_2$OCH$_2$CH(OH)CH$_2$OH

5. Acrylation

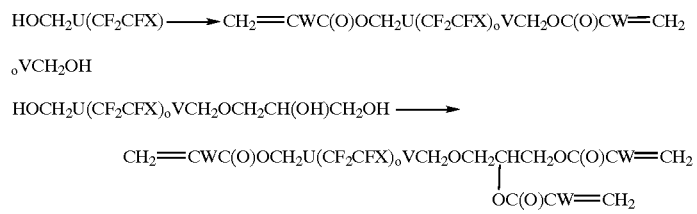

-continued

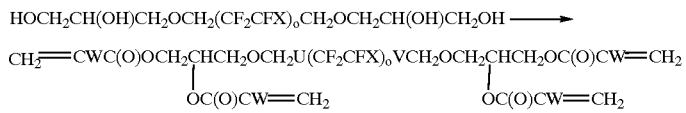

Suitable starting materials are polymers having the structure —[CH$_2$CYZ(CF$_2$CFX)$_n$]$_m$—, wherein X and Y=F, Cl, or Br; X and Y may be same or different; Z=H, F, Cl, Br, or an alkyl or perfluoroalkyl containing about 1 to about 10 carbons; n=an integer larger than about 1, preferably between about 2 to about 50, and most preferably from about 2 to about 10; and m is an integer between about 2 to about $10^5$, and most preferably about 10 to about $10^4$. The polymer has an average molecular weight of from about 500 to about 1×$10^6$, and preferably from about 1000 to about 1×$10^5$. These polymers can be obtained from copolymerization of a fluorinated vinyl monomer, CF$_2$=CFX, with another vinyl comonomer containing at least two hydrogen atoms, CH$^2$=CYZ; wherein X, Y, Z are defined as before. Suitable fluorinated vinyl monomers include, tetrafluoroethylene, chlorotrifluoroethylene, and bromotrifluoroethylene. Suitable vinyl comonomers include vinylidene fluoride, vinyl fluoride, vinyl chloride, vinylidene chloride, vinyl bromide, and 1-chloro-1-fluoro ethylene. One particularly suitable polymer is a copolymer of chlorotrifluoroethylene, CF$_2$=CFCl, with vinylidene fluoride, CH$_2$=CF$_2$, commercially available as ACLAR® resin from AlliedSignal Inc.

The sequence length, n, of the monomer CF$_2$=CFX determines the size of the final product. Since most of the copolymers —[CH$_2$CYZ(CF$_2$CFX)$_n$]$_m$—, are made by a free radical process, the sequence length of CF$_2$=CFX is usually not a distinct number but a distribution around a certain value. The monomer materials obtained from this invention, therefore, are mixtures of structural analogs containing a distribution of n around a certain number.

The first step in the method for preparing the halofluorinated multifunction monomers of the present invention is dehydrohalogenation of the starting material. As used herein, the dehydrohalogenation process may be thermally or chemically induced. Thermally induced dehydrohalogenation can be conducted from about 100° to about 500° C., at normal atmosphere or under vacuum, and with or without a catalyst. Preferably, thermo-dehydrohalogenation occurs at a temperature of from about 300° to about 450° C., and under a vacuum of about 10–50 torr. If a catalyst is used, it is typically present in an amount of from about 1% to about 20% of the polymer and comprises inorganic salts or oxides of a multivalent metal. Preferred catalysts include copper sulfate, copper chloride, barium sulfate, magnesium sulfate, manganese sulfate, barium oxide, copper oxide, magnesium oxide, manganese oxide, zinc oxide, and vanadium oxide. The thermo-dehydrohalogenation process may be conducted in solution, suspension, or most preferably, in bulk.

Alternatively, dehydrohalogenation may be chemically induced and, if so, a base compound is required. Suitable bases may be organic or inorganic and include primary, secondary, and tertiary amines; metal hydroxides, and alkali metal alkoxides. Preferred bases include trialkylamine, sodium hydroxide, potassium hydroxide, sodium or potassium t-butoxide, and sodium or potassium methoxide. The chemical dehydrohalogenation process may be conducted in solution, suspension, or bulk.

As is well known in the art, dehydrohalogenation is a standard process in organic chemistry. In particular, the dehydrohalogenation process in fluoroelasotomer containing chlorotrifluoroethylene and vinylidene fluoride monomer units is known; see for example, Paciorek et al., *Jour. Polymer Science*, 45:405–413 (1960). A special feature of the present invention is the formation of HX and HY in the dehydrohalogenation process (as X and Y are both halogens) which results in a unsaturated polymer having the formula —[CA=CEU(CF$_2$CFX)$_o$VCG=CM]$_m$—. This polymer is actually a mixture of the following structures:

—[CH=CZ(CF$_2$CFX)$_n$CH=CZ]$_m$—,
—[CH=CZ(CF$_2$CFX)$_{n-1}$CF$_2$CF=CH]$_m$—,
—[CF=CHCYZ(CF$_2$CFX)$_{n-1}$CF$_2$CF=]$_m$—, and
—[CF=CHCYZ(CF$_2$CFX)$_n$CH=CZ]$_m$—;

wherein X and Y=F, Cl, or Br; X and Y may be same or different; Z=H, F, Cl, Br, or an alkyl or perfluoroalkyl containing from about 1 to about 10 carbons; n=an integer larger than about 1, preferably between about 2 and about 50, and most preferably from about 2 to about 10; m is an integer between about 2 and about $10^5$, preferably from about 10 to about $10^4$; A and G=H or F; A and G may be same or different; E and M=H or Z; E and M may be same or different; o=n or n=l; U=CYZ or nothing; and V=CF$_2$ or nothing. The distribution of the four components in the mixture depends on the relative ease of elimination of HX and HY.

Thereafter, the double bond obtained from the dehydrohalogenation step is oxidized to a α, 107 -dicarboxylic acid and its ester derivatives. Oxidation of carbon-carbon double bond and in particular, the oxidation of partially fluorinated double bond, is known in the chemical arts; see, for example Hudlicky et al., *Chemistry of Organic Fluorine Compounds II*, p. 321, American Chem. Soc., Washington, D.C., 1995. Suitable oxidizing agents include oxygen, ozone, sodium or potassium persulfate, sodium or potassium permanganate, ruthenium tetroxide, sodium or potassium hypochlorite, sodium or potassium chlorate, sodium iodate, tetraalkyl ammonium permanganate, sodium or potassium dichromate, and chromium oxide. Preferred oxidizing agents include ozone, sodium or potassium persulfate, sodium or potassium permanganate, tetraalkyl ammonium permanganate, sodium or potassium hypochlorite, and sodium or potassium dichromate. The oxidation reaction can be carried out in solution, suspension, or bulk at a temperature range of from room temperature to about 300° C. A preferred oxidation condition is a solution reaction at a temperature of under about 150° C. The oxidation product can be either a α, ω-dicarboxylic acid or its ester derivatives, depending upon the oxidation reaction. The oxidation product may be thus represented by the formula RO$_2$CU(CF$_2$CFX)$_o$VCO$_2$R, and consists of a mixture of the following compounds: RO$_2$C(CF$_2$CFX)$_n$CO$_2$R; RO$_2$CCYZ(CF$_2$CFX) $_n$CO$_2$R; RO$_2$C(CF$_2$CFX)$_{n-1}$CF$_2$CO$_2$R; and RO$_2$CCYZ(CF$_2$CFX)$_{n-1}$CF$_2$CO$_2$R; wherein R=H or an alkyl containing about 1 to about 10 carbons and U, V, X, Y, Z, n and o are defined as before. The α, ω-dicarboxylic acid or ester derivative is itself a polymerization monomer which can be used to make special polyesters, polyamides, and other polymers.

The foregoing process to produce the α, ω-dicarboxylic acids or ester derivatives is far less cumbersome than the prior art process which are described, for example in copending U.S. Ser. No. 08/842,783, the disclosure of which is expressly incorporated herein by reference. Typical of the prior art production of α, ω-dicarboxylic acids ester derivatives with halofluorinated backbones is the scheme:

1. Telomerization

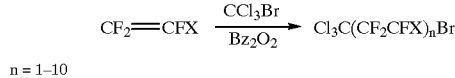

n = 1–10

2. Hydrolysis

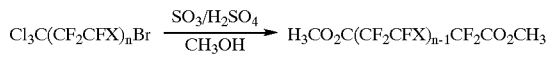

wherein X=Cl or Br; n=1–10; and Y=H, F, Cl, $CF_3$, or $CH_3$. Halofluorinated α, ω-dicarboxylic acids or ester derivatives prepared by the prior art methods are generally derivatized into polyols and eventually into acrylates by procedures which are known in the art.

Turning back to the present invention, the α, ω-dicarboxylic acid or esters having a halofluorinated alkylene backbone may be further reduced to a α, ω-diol by typical organic procedures which are readily available to the skilled artisan. The α, ω-diol thus formed is represented by the formula $HOCH_2U(CF_2CYZ)_oVCH_2OH$, wherein U, V, Y, Z, n and o are defined as before. Suitable reducing agents include boranes, 9-borabicyclo[3.3.1]nonane (9-BBN), lithium or sodium borohydride, lithium aluminum hydride, dialkyl aluminum hydride, aluminum hydride, lithium hydride, and alkyl lithium borohydride. Preferably, the reducing agent is aluminum hydride, sodium borohydride, or borane. The most preferred reducing agent for the α, ω-dicarboxylate ester, $RO_2CU(CF_2CFX)_oVCO_2R$, is aluminum hydride; see for example, copending application U.S. Ser. No. 08/842,783, the disclosure of which is expressly incorporated herein by reference.

The α, ω-diol containing halofluorinated alkylene chain, is by itself a polymerization monomer which can be used to make special polyesters, polycarbonates, and other polymers.

The α, ω-diol containing halofluorinated alkylene chain may be further derivatized to triol, tetraol, or other multi-functional alcohols which may be used directly as condensation monomers. Such conversion is known in the art; see for example, Turri et al., *Jour. Polymer Science. Part A: Polymer Chemistry*, 34:3263 (1966).

Alternatively, the di-, tri-, and tetra-ols may be further derivatized to corresponding di-, tri-, and tetra-acrylates by known procedures. These di-, tri- and tetra-acrylates are represented by the formulas:

$CH_2$=$CWC(O)OCH_2U(CF_2CFX)_oVCH_2OC(O)CW$=$CH_2$;

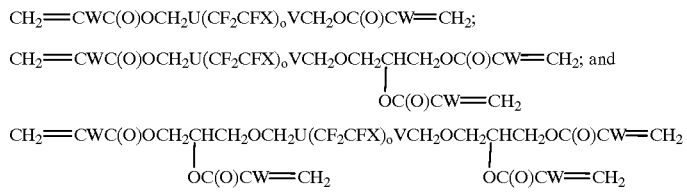

wherein U, V, X, Y, Z, n and o are defined as above and W=H, F, Cl, $CH_3$ or $CF_3$. The di-, tri-, and tetra-acrylates thus formed may be thermopolymerized or photocured in the presence of a radical photoinitiator to form transparent polymers which are useful as optical waveguiding materials.

The following examples are presented to provide a more complete understanding of the invention. The specific techniques, conditions, materials, proportions and reported data set forth to illustrate the principals and practice of the invention are exemplary and should not be construed as limiting the scope of the invention.

EXAMPLE 1

Chemically-induced dehydrohalogenation was carried out with potassium hydroxide as the base by suspending 30 parts of ACLAR® 420 resin (available from AlliedSignal Inc.) in a solution comprising 300 parts of isopropanol and 20 parts of potassium hydroxide. ACLAR® 420 is a copolymer of chlorotrifluoroethylene (CTFE) and vinylidene fluoride (VF2) containing 15 mol % of VF2 in the polymer and having a molecular weight of $1 \times 10^4$. After refluxing for 6–8 hours, the mixture was poured into 500 parts of water and extracted 3 times with 200 parts of ethyl ether and the ether layer removed ("ether workup"). The product was then subject to analytical characterization in which infrared analysis yielded a strong peak at wave numbers ($cm^{-1}$) 3350–2800 due to the C—H bond (C—H), a strong peak at 1650–1580 due to the C=C bond (C=C), and a very strong peak at 1200–1050 due to the C—F bond (C—F). $^{19}$F NMR analysis with $CF_3COOH$ as the standard yielded [δ] a broad peak at 30–50 ppm, which demonstrates the existence of $CF_2$ and CF in the compound. Elemental analysis indicated that the compound comprised: C=30.10%; Cl=16.60%; and F=44.59%.

EXAMPLE 2

The chemical dehydrohalogenation product of Example 1 was oxidized by dissolving 20 parts of the product in 300 parts of acetone and cooling the resultant solution to 1–5° C. with an ice bath. Thereafter, approximately 18 parts of potassium permanganate was added until a purple color was obtained, the solution was stirred for another hour, 50 parts of water was added, and sulfer dioxide gas was bubbled through the solution until a clear color was obtained. The acetone was removed resulting in 17 parts of the final product which comprised a pale yellow liquid. The final product was characterized as follows: IR (film, $cm^{-1}$)= 3500–2800 (very strong, OH), 1770–1730 (very strong, C=O), 1210–1100 (very strong, C–F); $^{19}$F NMR [δ($CF_3COOH$ as standard) ppm]=30–50 ppm (broad peak, $CF_2$ and CF); Elemental Analysis (%): C=28.52; Cl=17.20; F=41.12; average molecular weight (as measured by vapor pressure osmometry "VPO")=617.

EXAMPLE 3

Chemically induced dehydrohalogenation was carried out with triethylamine as a base. 10 parts of ACLAR® 420 resin (molecular weight $3 \times 10^5$) in 20 parts of dimethylformamide was added to 8 parts of triethyl amine at room temperature.

The mixture was warmed to 60° C. for 2 hours, and then poured into 500 parts of water. The precipitate was washed with water and methanol to give 9 parts of the dehydrohalogenated polymer.

EXAMPLE 4

The dehydrohalogenated polymer from Example 3 was oxidized by suspending 10 parts of the polymer in 200 parts of acetone and cooling to 1–5° C. Thereafter, approximately 9 parts of potassium permanganate was added until a purple color was obtained, the solution was stirred for another hour, 50 parts of water was added, and sulfur dioxide was bubbled through the solution to breach out the color. The acetone was removed and 10.6 parts of the pale yellow liquid product had similar IR and 19-NMR characterizations as Example 2. The average molecular weight of the product (VPO)=651.

EXAMPLE 5

Thermally-induced dehydrohalogenation was carried out with copper sulfate as a catalyst by heating 28 parts of ACLAR® 420 resin and 1 part of copper sulfate to 350–400° C. under a vacuum of 20 Torr while stirring. Characterization of the liquid distillate gave the following results.

IR (film, cm$^{-1}$)=1790 (strong,—CF=CF—), 1360 (strong), 1320 (strong), 1200–1100 (very strong, C—F), 970(strong), 900(strong); $^{19}$F NMR [δ(CF$_3$COOH standard) ppm]=29–36 (broad), 37.5–40 (broad), 43.0(strong).

EXAMPLE 6

13.5 parts of the dehydrohalogenation product from Example 5 was oxidized to a liquid diacid by the procedure described in Example 2. Characterization of the product gave the following results.

IR (film, cm$^{-1}$)=2700–3250 (strong, O—H), 1750–1780 (strong, C=O), 1120–1180 (very strong, C—F), 960 (strong); $^{19}$F NMR [δ(CF$_3$COOH standard) ppm]: 29–34 (broad), 35–37 (broad), 39(medium); $^1$H NMR [δ, ppm]: 8.5 (strong, COOH); Elemental Analysis (%): C: 27.11; Cl: 120.63; F: 45.45; average molecular weight (VPO)=651.

EXAMPLE 7

Thermally-induced dehydrohalogenation of ACLAR® 3000 resin was carried out with copper sulfate as the catalyst by stirring 30 parts of ACLAR® 3000 resin and 1.5 parts of copper sulfate with heat to 350–400° C. under a vacuum of 20 Torr. ACLAR® 3000 is a copolymer of chlorotrifluoroethylene (CTFE) and vinylidene fluoride (VF2) containing 3.5 mol. % of VF2 in the polymer and having a high molecular weight grade. Characterization of the liquid distillate gave the following results.

IR (film, cm$^{-1}$)=1770 (strong, —CF=CF—), 1370 (strong), 1300 (strong), 1200–1100 (very strong, C—F), 970 (strong); $^{19}$F NMR [δ(CF$_3$COOH standard) ppm]=10.0 (medium, ClCF$_2$), 12.0 (tall, —CF=CF—), 30 (medium, CF$_2$), 38.5 (medium, CF$_2$=), 50 (medium, CF$_2$).

EXAMPLE 8

15 parts of the dehydrohalogenation product from Example 7 was oxidized to a liquid diacid by the procedure described in Example 2. 7.1 parts of the liquid product was obtained. Characterization of the product gave the following results.

IR (film, cm$^{-1}$)=2700–3250 (strong, O—H), 1750–1780 (strong, C—O), 1120–1180 (very strong, C—F), 960 (strong); $^{19}$F NMR [δ(CF$_3$COOH standard) ppm]: −10.5 (medium, ClCF$_2$), 30.0 (medium, CF$_2$), 49.5 (medium, CF$_2$); Elemental Analysis (%) C=24.38; Cl=23.62; F=42.21; average molecular weight (VPO)=610.

EXAMPLE 9

The diacid from Example 2 was esterified by refluxing for 8 hours 100 parts of dried methanol containing 44 parts of the diacid mixture obtained from Example 2 and 1 part of concentrated H$_2$SO$_4$. The mixture was poured into 300 parts of water and extracted with 3 times 30 parts of ether. The ether was removed and 41 parts of crude diesters was obtained. After silica column chromatographic purification (Merck #60), 33 parts of diesters was collected. The mixture of diesters: CH$_3$OC(O)(CF$_2$CFCl)$_n$CF$_2$CO$_2$CH$_3$ (n=3, 4, 5, 6) and CH$_3$OC(O)CF$_2$(CF$_2$CFCl)$_m$CF$_2$CO$_2$CH$_3$ (m=2, 3, 4, 5, 6), was identified by GC-MS, $^1$H NMR and GC with standard samples.

EXAMPLE 10

The ester derivative from Example 9 was reduced to a diol by slowly adding 16.5 parts of the diester mixture obtained in Example 9 in 50 parts of tetrahydrofuran to 200 parts of 0.91 M AlH$_3$ in tetrahydrofuran while stirring at 0° C. After one hour, the excessive hydride was carefully hydrolyzed with 10 parts of 1:1 mixture of tetrahydrofuran and water, subject to ether workup and distillation, and 14 parts of the diol mixture obtained. Characterization of this product is consistent with the indicated structure.

EXAMPLE 11

A diol was derivitized to an acrylate by mixing 80 parts of the diol mixture described in Example 10 with 55 parts of triethylamine and 100 parts of methylene chloride and cooling to 0° C. 55 parts of freshly distilled acryloyl chloride in 100 parts of methylene chloride was slowly added to the solution while stirring under nitrogen. The stirring continued for an additional 24 hours, the temperature returned to ambient and the mixture was treated with water and worked up with ethyl ether. The crude product thus obtained was purified by silica gel column chromatography (Merck #60) eluted with petroleum either and ethyl acetate mixture (50:1, respectively). The characterization result of the purified diacrylate mixture is consistent with the indicated structure.

EXAMPLE 12

A diol was derivitized into a diacrylate by mixing 32.2 parts of the diol mixture described in Example 10 with 35.4 parts acryloyl chloride and 0.1 part of 4-methoxyphenol. Reflux was carried out at 90° C. (oil bath) for 8 hr. The excess acryloyl chloride was recovered by vacuum distillation, with the residue being diacrylate that could be decolorized with activated carbon. Small amount of polymer was removed on a 0.1 μ filter. Yield of the diacrylate was 90%. The characterization result is consistent with the indicated structure.

EXAMPLE 13

The diacrylate mixture from Example 11 was formed into a transparent film by mixing it with 2.0 wt. % of benzodimethyl ketal (Irgacure 651) at 50° C. to make a homogeneous composition which was then pressure-filtered through a 0.2 micron PTFE membrane. The composition was spin-coated onto a quartz plate to form a 2 micron thick liquid layer which irradiated for 5 seconds under medium pressure mercury UV lamp in nitrogen to obtain a tough transparent solid film.

Having thus described the invention in rather full detail, it will be understood that such detail need not be strictly adhered to but that further changes and modifications may suggest themselves to one skilled in the art, all falling within the scope of the invention as defined by the subjoined claims.

We claim:

1. A method for preparing halofluorinated multifunctional monomers comprising the steps of:

(a) subjecting a first polymer which is the reaction product of a fluorinated vinyl monomer and a vinyl comonomer, to dehydrohalogenation to form a second polymer;

(b) treating said second polymer with an oxidizing agent to form an oxidation product consisting of α, ω-dicarboxylic acid or an ester derivative thereof; and (c) treating said oxidation product with a reducing agent to form a reduction product consisting of a α, ω-diol.

2. The method of claim 1, wherein said reduction product is converted to an acrylate.

3. The method of claim 1, wherein said reduction product is further derivatized to a triol, tetraol or other multifunctional alcohol.

4. The method of claim 3, wherein said triol, tetraol or other multifunctional alcohol is converted to an acrylate.

5. The method of claim 1, wherein said first polymer has an average molecular weight from about 500 to about $1 \times 10^6$.

6. The method of claim 1, wherein said first polymer has an average molecular weight from about 1000 to about $1 \times 10^5$.

7. The method of claim 1, wherein said first polymer has the structure —[CH$_2$CYZ(CF$_2$CFX)$_n$]$_m$— wherein X and Y=F, Cl or Br; X and Y may be the same or different; Z=H, F, Cl, Br, alkyl or perfluoroalkyl containing from about 1 to about 10 carbon atoms; n=an integer larger than about 1; and m is an integer between about 2 and about $10^5$.

8. The method of claim 7, wherein for said first polymer, n is between about 2 to about 50.

9. The method of claim 7, wherein for said polymer, n is between about 2 to about 10.

10. The method of claim 7, wherein said first polymer, m is between about 2 to about $10^5$.

11. The method of claim 7, wherein for said first polymer, m is between about 10 to about $10^4$.

12. The method of claim 1, wherein said first polymer is obtained from the copolymerization of a fluorinated vinyl monomer having the formula CF$_2$=CFX with a vinyl monomer having the formula CH$_2$=CYZ wherein X and Y=F, Cl or Br; X and Y may be the same or different; and Z=H, F, Cl, Br, alkyl or perfluoroalkyl containing from about 1 to about 10 carbon atoms.

13. The method of claim 1, wherein said first polymer is obtained from the copolymerization of chlorotrifluoroethylene and vinylidene fluoride.

14. The method of claim 1, wherein said dehydrohalogenation is induced by a method comprising heat or base.

15. The method of claim 1, wherein said second polymer has the formula —[CA=CEU(CF$_2$CFX)$_o$VCG=CM]$_m$— wherein X and Y=F, Cl or Br; X and Y may be the same or different; Z=H, F, Cl, Br, alkyl or perfluoroalkyl having from about 1 to about 10 carbon atoms; n=an integer larger than about 1; m=an integer between about 2 and about $10^5$; A and G=H or F; A and G may be the same of different; E and M=H or Z; E and M may be the same of different; 0=n or n−1; U=CYZ or nothing; V=CF$_2$ or nothing.

16. The method of claim 1, wherein said oxidizing agent is potassium permanganate.

17. The method of claim 1, wherein said oxidation product has the formula RO$_2$CU(CF$_2$CFX)$_o$VCO$_2$R, wherein R=H or an alkyl compound having from about 1 to about 10 carbon atoms; X and Y=F, Cl or Br; X and Y may be the same or different; Z=H, F, Cl, Br, alkyl or perfluoroalkyl having from about 1 to about 10 carbon atoms; n=an integer larger than about 1; m=an integer between about 2 and about $10^5$; A and G=H or F; A and G may be the same of different; E and M=H or Z; E and M may be the same or different; 0=n or n−1; U=CYZ or nothing; V=CF$_2$ or nothing.

18. The method of claim 1 further comprising using the oxidation product of claim 1 to make polyester, polyamide or other polymers.

19. The method of claim 1, wherein said reduction product has the formula HOCH$_2$U(CF$_2$CYZ)$_o$VCH$_2$OH wherein X and Y=F, Cl or Br; X and Y may be the same or different; Z=H, F, Cl, Br, alkyl or perfluoroalkyl having from about 1 to about 10 carbon atoms; n=an integer larger than 1; m=an integer between about 2 and about $10^5$; A and G=H or F; A and G may be the same of different; E and M=H or Z; E and M may be the same of different; 0=n or n−1; U=CYZ or nothing; V=CF$_2$ or nothing.

20. The method of claim 1, wherein said reducing agent is aluminum hydride.

21. The method of claim 1 further comprising using the reduction product of claim 1 to make polyester, polycarbonate, and other polymers.

22. A method for preparing halofluorinated multifunctional monomers comprising the steps of:

(a) subjecting a first polymer having a structure of —[CH$_2$CYZ(CF$_2$CFX)$_n$]$_m$— wherein X and Y=F, Cl or Br; X and Y may be the same or different; Z=H, F, Cl, Br, alkyl or perfluoroalkyl containing from about 1 to about 10 carbon atoms; n=an integer larger than about 1; and m is an integer between about 2 and about $10^5$, to dehydrohalogenation to form a second polymer;

(b) treating said second polymer with an oxidizing agent to form an oxidation product consisting of an α, ω-dicarboxylic acid or an ester derivative thereof; and (c) treating said oxidation product with a reducing agent to form a reduction product consisting of a α, ω-diol.

* * * * *

UNITED STATES PATENT AND TRADEMARK OFFICE
CERTIFICATE OF CORRECTION

PATENT NO. : 6,166,156                                              Page 1 of 1
DATED      : December 26, 2000
INVENTOR(S) : Chengjui Wu, Baopei Xu, and James T Yardley It is certified that error appears in the above-identified patent and that said Letters Patent is hereby corrected as shown below:

Column 4,
Line 29, delete "n=1" and insert -- n-1 --.

Column 10,
Line 8, delete"O=n" and insert -- o = n --.
Lines 21-22, delete "...A and G=H or F; A and G may be the same of different; E and M=H or Z; E and M may be the same or different...."
Line 22, delete "O=n" and insert -- o = n --.
Lines 31-33, delete "...A and G=H or F; A and G may be the same of different; E and M=H or Z; E and M may be the same of different...."
Line 33, delete "O=n" and insert -- o = n --.

Signed and Sealed this

Twenty-second Day of January, 2002

*Attest:*

*Attesting Officer*

JAMES E. ROGAN
*Director of the United States Patent and Trademark Office*